United States Patent
Baumgart et al.

(10) Patent No.: US 10,332,256 B2
(45) Date of Patent: Jun. 25, 2019

(54) CONTRAST FLOW IMAGING SYSTEM

(71) Applicant: Siemens Medical Solutions USA, Inc., Malvern, PA (US)

(72) Inventors: John Baumgart, Hoffman Estates, IL (US); Martin Trini, Schaumburg, IL (US)

(73) Assignee: Siemens Healthcare GmbH, Erlangen (DE)

(*) Notice: Subject to any disclaimer, the term of this patent is extended or adjusted under 35 U.S.C. 154(b) by 209 days.

(21) Appl. No.: 15/425,677

(22) Filed: Feb. 6, 2017

(65) Prior Publication Data

US 2018/0225825 A1 Aug. 9, 2018

(51) Int. Cl.
| | |
|---|---|
| *G06T 7/00* | (2017.01) |
| *G06T 5/50* | (2006.01) |
| *G06T 7/30* | (2017.01) |
| *G06T 7/73* | (2017.01) |
| *A61B 6/00* | (2006.01) |

(52) U.S. Cl.
CPC ............ *G06T 7/0014* (2013.01); *A61B 6/481* (2013.01); *A61B 6/504* (2013.01); *G06T 5/50* (2013.01); *G06T 7/30* (2017.01); *G06T 7/73* (2017.01); *A61B 6/4441* (2013.01); *A61B 6/4464* (2013.01); *G06T 2207/10016* (2013.01); *G06T 2207/10116* (2013.01); *G06T 2207/20221* (2013.01); *G06T 2207/20224* (2013.01); *G06T 2207/30104* (2013.01)

(58) Field of Classification Search
USPC .......................................... 382/128, 130–132
See application file for complete search history.

(56) References Cited

U.S. PATENT DOCUMENTS

| | | | |
|---|---|---|---|
| 8,050,474 B2 * | 11/2011 | Baumgart | ................. G06T 5/50 382/130 |
| 8,848,996 B2 | 9/2014 | Baumgart | |
| 10,083,511 B2 * | 9/2018 | Baumgart | ............. G06T 7/0038 |
| 2011/0235885 A1 | 9/2011 | Rauch | |
| 2012/0099768 A1 * | 4/2012 | Helm | ................... A61B 6/4405 382/128 |
| 2016/0089095 A1 | 3/2016 | Baumgart | |
| 2018/0078226 A1 * | 3/2018 | Helm | ................... A61B 6/4405 |

* cited by examiner

*Primary Examiner* — Ishrat I Sherali

(57) ABSTRACT

A system and method includes reception of a plurality of fill frames of a patient volume, each of the plurality of fill frames depicting a contrast medium within the patient volume at a respective time, identification, for each pixel location of the fill frames, of a fill frame whose pixel at the pixel location is associated with a pixel value which represents a greater level of contrast medium than the pixel values of pixels at the pixel location within the others of the plurality of fill frames, generation of a peak contrast fill frame corresponding to each fill frame, the peak contrast fill frame corresponding to a given fill frame including, at pixel locations for which the given fill frame was identified, pixels associated with pixel values of the given fill frame, and storage of the plurality of peak contrast fill frames.

18 Claims, 8 Drawing Sheets

CONTRAST FLOW IMAGING SYSTEM

BACKGROUND

Contrast media are used to enhance the contrast of patient vasculature within x-ray images. For example, a contrast medium is introduced into a patient volume (e.g., via intravenous injection) and an x-ray image of the volume is acquired while the medium is located within the volume. In the x-ray image, structures which contain the medium (e.g., veins and arteries) appear darker than they would otherwise appear.

X-ray images may be successively acquired as a contrast medium passes through patient vasculature. Together, these images portray the flow of contrast over time and may be displayed in rapid succession to animate the flow of contrast. However, these images do not provide sufficient information relating to peak contrast values within the images.

BRIEF DESCRIPTION OF THE DRAWINGS

The construction and usage of embodiments will become readily apparent from consideration of the following specification as illustrated in the accompanying drawings, in which like reference numerals designate like parts, and wherein.

DETAILED DESCRIPTION

The following description is provided to enable any person in the art to make and use the described embodiments and sets forth the best mode contemplated for carrying out the described embodiments. Various modifications, however, will remain readily apparent to those in the art.

Some embodiments facilitate the generation of image frames showing peak contrast levels within patient vasculature. According to some embodiments, image frames of a patient volume are acquired as a contrast medium passes through the volume. Each of the acquired image frames is converted to a "peak contrast" image frame. For each pixel of a given image frame, the pixel value is unchanged in the corresponding peak contrast frame if the pixel value represents a peak contrast level for that pixel's location amongst all of the acquired image frames. Other pixels of the corresponding peak contrast frame are assigned other pixel values (e.g., pixel values of pixels located at the same pixel locations of a mask image frame).

Figure 1:
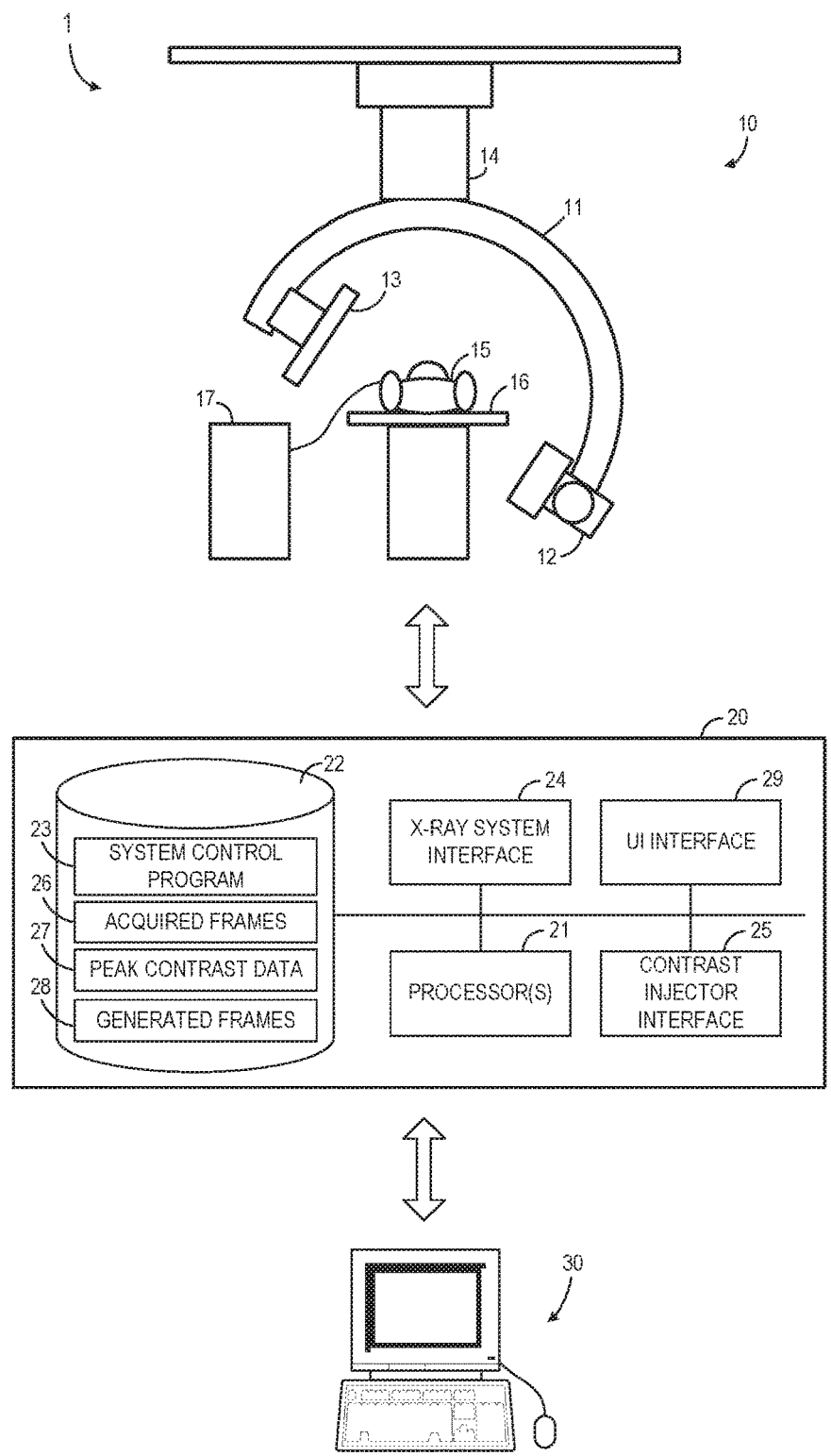
FIG. 1 illustrates a system according to some embodiments.

FIG. 1 illustrates system 1 according to some embodiments. System 1 includes x-ray imaging system 10, control and processing system 20, and operator terminal 30. Generally, and according to some embodiments, x-ray imaging system 10 introduces contrast medium into a patient volume and acquires x-ray images of the patient volume. Control and processing system 20 controls x-ray imaging system 10 and receives the acquired images therefrom. Control and processing system 20 processes the images as described below and provides the processed images to terminal 30 for display thereby. Such processing may be based on user input received by terminal 30 and provided to control and processing system 20 by terminal 30.

X-ray imaging system 10 comprises C-arm 11 on which radiation source 12 and radiation detector 13 are mounted. C-arm 11 is mounted on support 14 and is configured to translate clockwise or counter-clockwise with respect to support 14. This translation rotates radiation source 12 and radiation detector 13 around a central volume while maintaining the physical relationship therebetween. Embodiments are not limited to C-arm-based imaging systems.

Radiation source 12 may comprise any suitable radiation source, including but not limited to a Gigalix™ x-ray tube. In some embodiments, radiation source 12 emits electron, photon or other type of radiation having energies ranging from 50 to 150 keV.

Radiation detector 13 may comprise any system to acquire an image based on received x-ray radiation. In some embodiments, radiation detector 13 is a flat-panel imaging device using a scintillator layer and solid-state amorphous silicon photodiodes deployed in a two-dimensional array. The scintillator layer receives photons and generates light in proportion to the intensity of the received photons. The array of photodiodes receives the light and records the intensity of received light as stored electrical charge.

In other embodiments, radiation detector 13 converts received photons to electrical charge without requiring a scintillator layer. The photons are absorbed directly by an array of amorphous selenium photoconductors. The photoconductors convert the photons directly to stored electrical charge. Radiation detector 13 may comprise a CCD or tube-based camera, including a light-proof housing within which are disposed a scintillator, a mirror, and a camera.

The charge developed and stored by radiation detector 13 represents radiation intensities at each location of a radiation field produced by x-rays emitted from radiation source 12. The radiation intensity at a particular location of the radiation field represents the attenuative properties of tissues lying along a divergent line between radiation source 12 and the particular location of the radiation field. The set of radiation intensities acquired by radiation detector 13 may therefore represent a two-dimensional projection image of these tissues.

Contrast injector 17 may comprise any known device or devices suitable to controllably introduce contrast medium into a patient volume. As described above, structures which contain contrast medium appear darker in x-ray images than they would otherwise appear. Contrast injector 17 may include a reservoir for each of one or more contrast media, and a patient interface such as medical-grade tubing terminating in a hollow needle.

System 20 may comprise any general-purpose or dedicated computing system. Accordingly, system 20 includes one or more processors 21 configured to execute processor-executable program code to cause system 20 to operate as described herein, and storage device 22 for storing the program code. Storage device 22 may comprise one or more fixed disks, solid-state random access memory, and/or removable media (e.g., a thumb drive) mounted in a corresponding interface (e.g., a USB port).

Storage device 22 stores program code of system control program 23. One or more processors 21 may execute system control program 23 to move C-arm 11, to move table 16, to cause radiation source 12 to emit radiation, to control detector 13 to acquire an image, to cause injector 17 to introduce contrast medium into a volume of patient 15, and to perform any other function. In this regard, system 20 includes x-ray system interface 24 and contrast injector interface 25 for communication with corresponding units of system 10.

Images acquired from system 10 are stored in data storage device 22 as acquired frames 26, in DICOM or another data format. Acquired frames 26 may consist of, in some embodiments, two-dimensional images of a patient volume which does not include a contrast medium (i.e., mask frames) and two-dimensional images of the patient volume including a contrast medium (i.e., fill frames). Each acquired frame 26 may be further associated with details of its acquisition, including but not limited to time of acquisition, imaging plane position and angle, imaging position, radiation source-to-detector distance, patient anatomy imaged, patient position, contrast medium bolus injection profile, x-ray tube voltage, image resolution and radiation dosage.

Processor(s) 21 may further execute system control program 23 to generate peak contrast data 27 and generated frames 28, embodiments of which will be described below. Generated frames 28 may be provided to terminal 30 via UI interface 29 of system 20. UI interface 28 may also receive input from terminal 30, which is used to control processing of acquired frames 26 as described below.

Terminal 30 may comprise a display device and an input device coupled to system 20. Terminal 30 displays acquired frames 26 and/or processed images 27 received from system 20 and may receive user input for controlling display of the images, operation of imaging system 10, and/or the processing of acquired frames 26. In some embodiments, terminal 30 is a separate computing device such as, but not limited to, a desktop computer, a laptop computer, a tablet computer, and a smartphone.

Each of system 10, system 20 and terminal 30 may include other elements which are necessary for the operation thereof, as well as additional elements for providing functions other than those described herein.

According to the illustrated embodiment, system 20 controls the elements of system 10. System 20 also processes images received from system 10. Moreover, system 20 receives input from terminal 30 and provides processed images to terminal 30. Embodiments are not limited to a single system performing each of these functions. For example, system 10 may be controlled by a dedicated control system, with the acquired frames being provided to a separate image processing system over a computer network or via a physical storage medium (e.g., a DVD).

Figure 2:
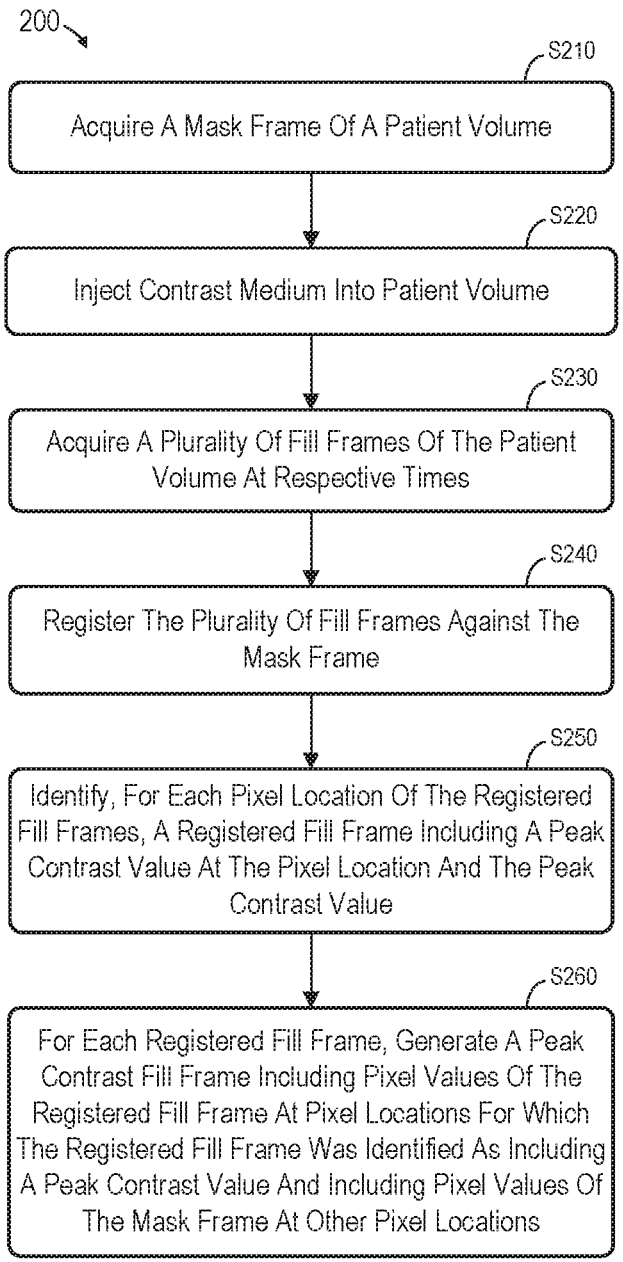
FIG. 2 is a flow diagram of process to generate images according to some embodiments.

FIG. 2 is a flow diagram of process 200 according to some embodiments. Process 200 and the other processes described herein may be performed using any suitable combination of hardware, software or manual means. Software embodying these processes may be stored by any non-transitory tangible medium, including a fixed disk, a floppy disk, a CD, a DVD, a Flash drive, or a magnetic tape. Examples of these processes will be described below with respect to the elements of system 1, but embodiments are not limited thereto.

It will be assumed that, prior to S210, the patient is positioned for imaging according to known techniques. For example, and with reference to the elements of system 1, patient 15 is positioned on table 16 to place a particular volume of patient 15 between radiation source 12 and radiation detector 13. System 20 may assist in adjusting table 16 to position the patient volume as desired. As is known in the art, such positioning may be based on a location of a volume of interest, on positioning markers located on patient 15, on a previously-acquired planning image, and/or on a portal image acquired after an initial positioning of patient 15 on table 16.

According to some embodiments, a mask frame is acquired at a desired projection angle at S210. The mask frame is acquired before introduction of a contrast medium into the patient volume. In some embodiments of S210, radiation source 12 is powered by a high-powered generator to emit x-ray radiation toward radiation detector 13 at the desired projection angle. The parameters of the x-ray radiation emission (e.g., timing, x-ray tube voltage, dosage) may be controlled by system control program 23 as is known in the art. Radiation detector 13 receives the emitted radiation and produces a set of data (i.e., a projection image). The projection image may be received by system 20 and stored among acquired frames 26 in either raw form or after any suitable pre-processing (e.g., denoising filters, median filters and low-pass filters).

Next, at S220, contrast medium is injected into the patient volume (e.g., into an artery of the patient volume). According to some embodiments of S220, system 20 instructs contrast injector 17 to introduce contrast medium into an artery of patient 15. The parameters of the medium introduction (e.g., flow rate, location, volume) may be controlled by system control program 23 as is known in the art.

A plurality of fill frames of the patient volume are acquired at S230. The fill frames are acquired from the same projection angle as was used during acquisition of the mask frame. Each of the plurality of fill frames is acquired at a respective time, such that each fill frame shows the injected contrast medium within the patient volume at a different time. Viewed as a whole, the fill frames illustrate movement of the contrast medium through the patient volume over time.

Each of the plurality of fill frames is registered against the mask frame at S240. Registration is intended to remove motion artifacts between the frames, by correcting for any relative motion of the patient between acquisitions of the frames. Any motion correction technique may be employed at S240.

Figure 3:
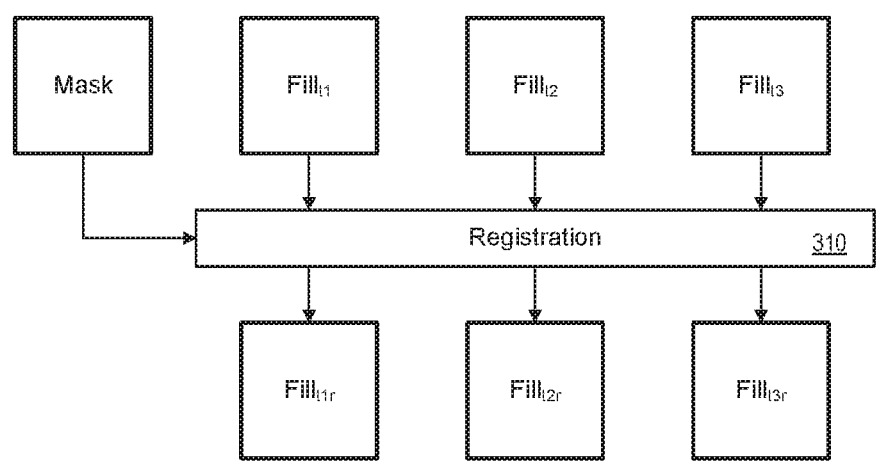
FIG. 3 illustrates a portion of a process to generate images according to some embodiments.

FIG. 3 illustrates registration at S240 according to some embodiments. A mask frame acquired at S210 is depicted along with three fill frames ($Fill_{f1}$, $Fill_{f2}$, $Fill_{f3}$) acquired at S230. For the present example, it is assumed that fill frame $Fill_{f1}$ was acquired at time t1, fill frame $Fill_{f2}$ was acquired at time t2, and fill frame $Fill_{f3}$ was acquired at time t3. Embodiments are not limited to three fill frames.

Fill frames $Fill_{f1}$, $Fill_{f2}$ and $Fill_{f3}$ may be registered against the mask frame by registration module 310 (e.g., processor-executable software code executed by computing hardware) as illustrated. The registration process results in three new fill frames, $Fill_{f1r}$, $Fill_{f2r}$ and $Fill_{f3r}$.

Figure 4:
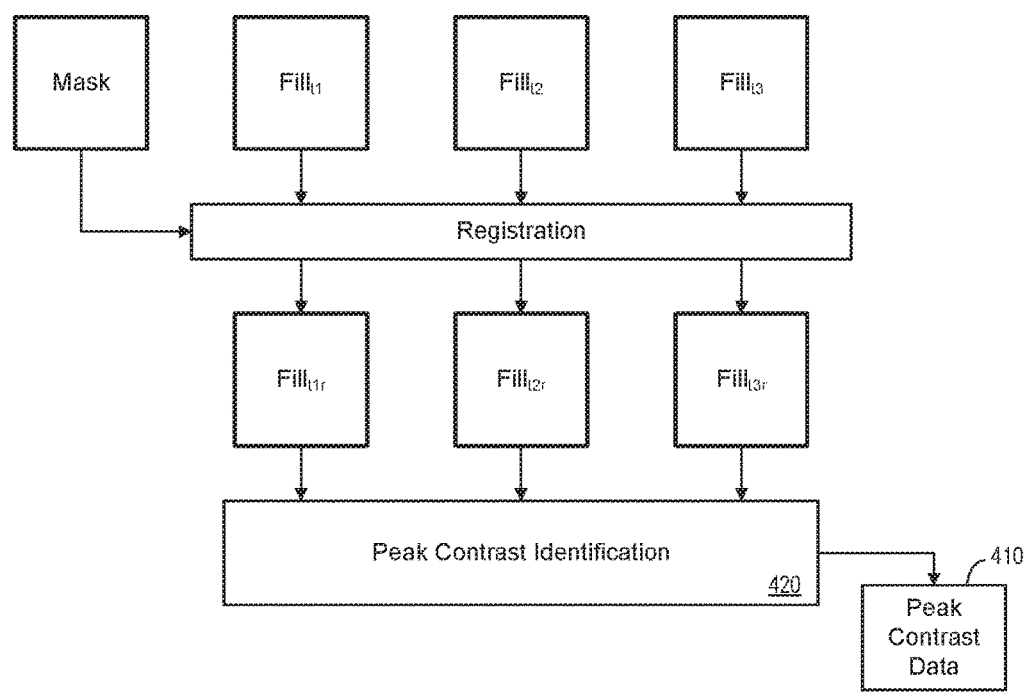
FIG. 4 illustrates a portion of a process to generate images according to some embodiments.

Returning to process 200, peak contrast values for each pixel location of the registered fill frames are identified at S250. Also identified are the registered fill frames which include the peak contrast value of each pixel location. The registered fill frame and peak contrast value which are identified for each pixel location may be stored in a data structure such as peak contrast data 410 of FIG. 4. Also illustrated is peak contrast identification module 420 which executes S250 according to some embodiments. Peak contrast identification module 420 may be implemented in hardware and/or processor executable software code.

Figure 5:
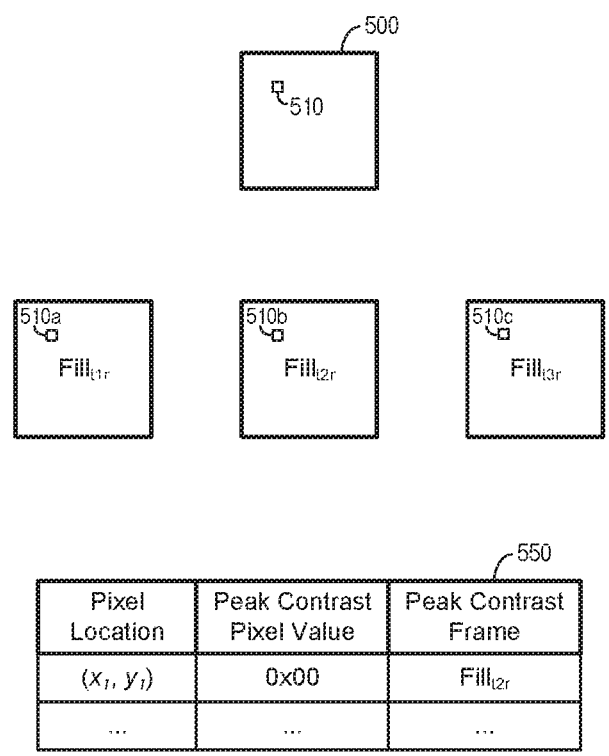
FIG. 5 illustrate identification of a peak contrast frame and a peak contrast pixel value for a pixel location according to some embodiments.

FIG. 5 illustrates S250 in additional detail according to some embodiments. Frame 500 is a dummy frame which is presented to illustrate the concept of "pixel location". Frame 500 shares the dimensions and pixel density, and therefore the same pixel locations, as each of registered fill frames $Fill_{t1r}$, $Fill_{t2r}$, and $Fill_{t3r}$. Pixel location 510 is also illustrated as pixel locations 510a, 510b and 510c of registered fill frames $Fill_{t1r}$, $Fill_{t2r}$, and $Fill_{t3r}$, respectively. Each of registered fill frames $Fill_{t1r}$, $Fill_{t2r}$, and $Fill_{t3r}$ includes a pixel at respective pixel locations 510a, 510b and 510c, and each of those pixels is associated with a pixel value.

Accordingly, for each pixel location (e.g., location 510), S250 identifies all the pixels at corresponding locations (e.g., locations 510a, 510b and 510c) of the fill frames, identifies one pixel of the identified pixels whose pixel value corresponds to the highest contrast level (i.e., peak contrast), and identifies the fill frame which includes the identified pixel. In some embodiments, a lower pixel value (e.g., a darker pixel) corresponds to a higher contrast level, while in other embodiments the relationship between pixel value and contrast level is direct (i.e., the higher the pixel value, the higher the contrast level).

Table 550 may comprise an implementation of peak contrast data structure 410, but embodiments are not limited thereto. Each row of table 550 includes a pixel location, a pixel value representing a peak contrast level at the location from all of the fill frames, and an identifier of the fill frame which includes a pixel at the pixel location having the peak contrast value. According to some embodiments of S250, one row of table 550 is generated and populated for each pixel location of the fill frames (e.g., each pixel location of dummy frame 500).

Any number or type of data structures suitable for relating the data described herein may be employed. According to some embodiments, the data structures comprise a peak contrast frame and a time map. Each pixel of the peak contrast frame is assigned the peak contrast pixel value of its respective pixel location among the fill frames. The peak contrast frame therefore encapsulates the data stored in the first two columns of table 550.

The time map may indicate a fill frame (or a timestamp corresponding to a fill frame) which includes the pixel having the peak contrast pixel value for a given pixel location. In this sense, the time map represents the data stored in the first and third columns of table 550.

Next, at S260, a peak contrast fill frame is generated for each registered fill frame. The pixels of a peak contrast fill frame which corresponds to a given registered fill frame have pixel values of the registered fill frame at pixel locations for which the registered fill frame was identified as including a peak contrast value. At other pixel locations, the pixels of the peak contrast fill frame have corresponding pixel values of the mask frame.

Figure 6:
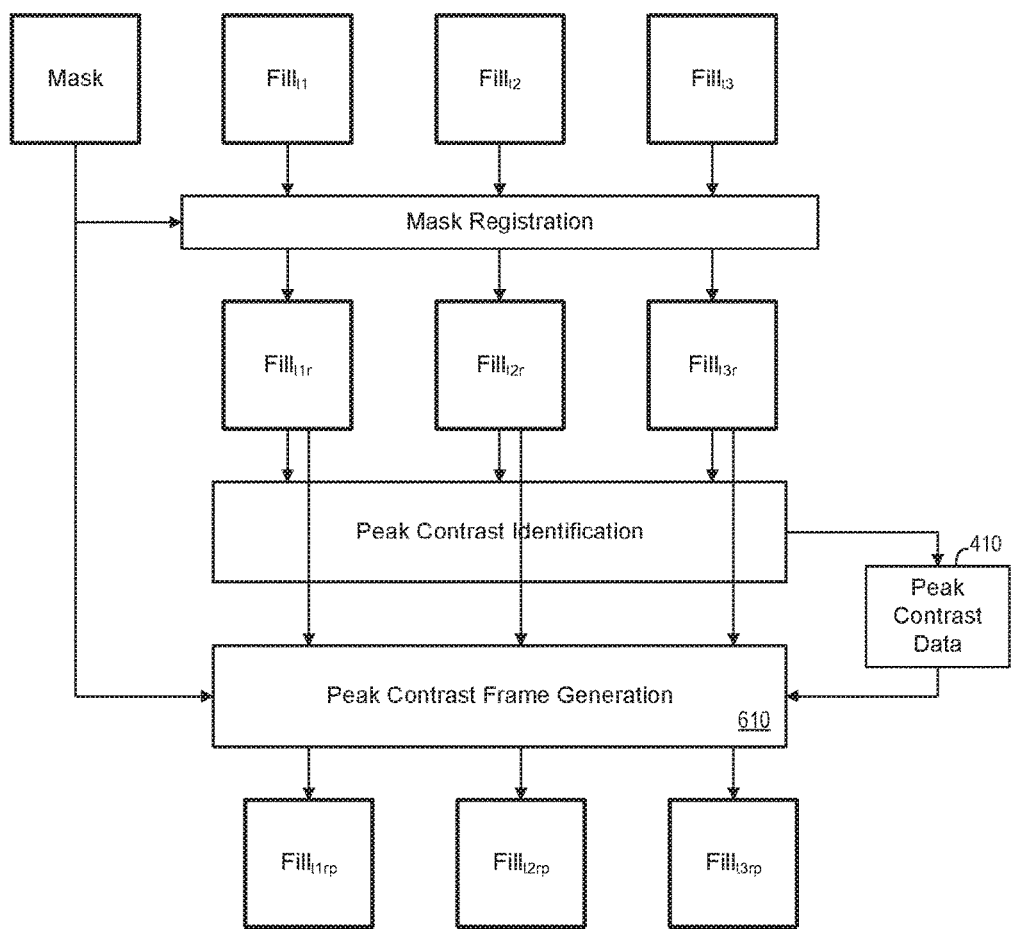
FIG. 6 illustrates a portion of a process to generate images according to some embodiments.

FIG. 6 illustrates peak contrast frame generation module 610, which generates peak contrast fill frames $Fill_{t1rp}$, $Fill_{t2rp}$ and $Fill_{t3rp}$ based on registered fill frames $Fill_{t1r}$, $Fill_{t2r}$ and $Fill_{t3r}$ and on peak contrast data 410. According to some embodiments of S260, peak contrast frame generation module 610 first generates a peak contrast fill frame based on registered fill frame $Fill_{t1r}$. To do so, module 610 identifies the pixel locations for which fill frame $Fill_{t1r}$ is identified as the peak contrast frame within peak contrast data 410. The values of pixels of fill frame $Fill_{t1r}$ at those pixel locations are simply assigned to the pixels of frame $Fill_{t1rp}$ which are located at the same pixel locations. These pixel values are identified in peak contrast data 550 as peak contrast pixel values for their respective pixel locations.

For the remaining pixel locations of peak contrast fill frame $Fill_{t1rp}$, peak contrast frame generation module 610 determines the values of pixels at those locations within the mask frame acquired at S210. The determined values are assigned to respective pixels of frame $Fill_{t1rp}$ at the remaining pixel locations.

Accordingly, a pixel located at a given pixel location of peak contrast fill frame $Fill_{t1rp}$ is assigned the same value as a pixel located in the same pixel location of frame $Fill_{t1r}$, if that pixel value is a peak contrast pixel value for the given location amongst all of the registered fill frames. If the pixel value is not a peak contrast pixel value for the given location amongst all of the registered fill frames, the pixel is assigned the same value as a pixel located in the same pixel location of the mask frame. Frames $Fill_{t2rp}$ and $Fill_{t3rp}$ may be generated similarly.

Figure 7:
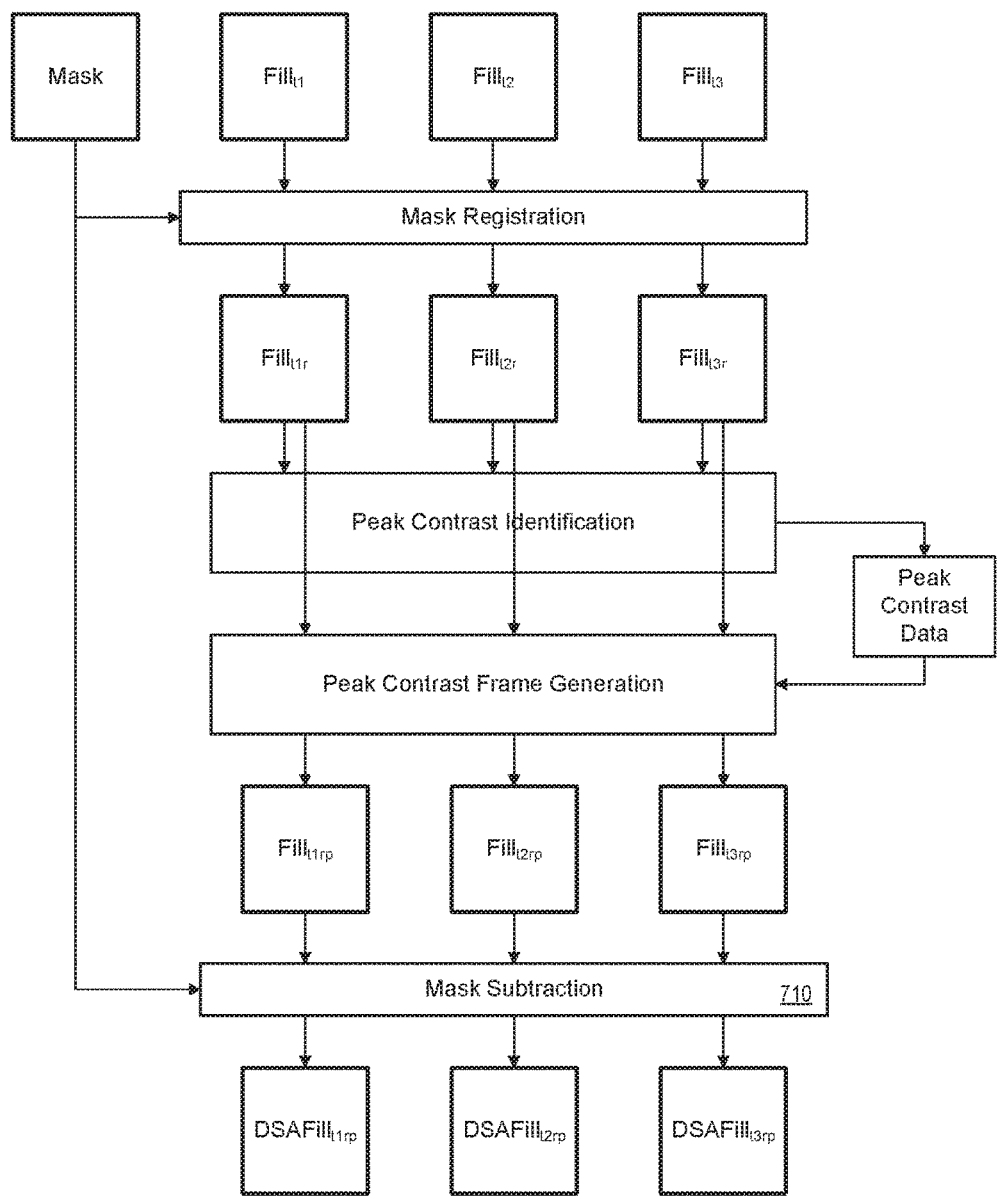
FIG. 7 illustrates a process to generate images according to some embodiments.

According to some embodiments, the mask frame is subtracted from each of peak contrast fill frames $Fill_{t1rp}$, $Fill_{t2rp}$ and $Fill_{t3rp}$ as illustrated in FIG. 7. In particular, mask subtraction module subtracts the mask frame from each of peak contrast fill frames $Fill_{t1rp}$, $Fill_{t2rp}$ and $Fill_{t3rp}$ to generate respective Digital Subtraction Angiography (DSA) frames $DSAFill_{t1rp}$, $DSAFill_{t2rp}$ and $DSAFill_{t3rp}$. Since frames $Fill_{t1rp}$, $Fill_{t2rp}$ and $Fill_{t3rp}$ consist of either pixels having peak contrast pixel values and pixels having pixel values of the mask frame, the frames $DSAFill_{t1rp}$, $DSAFill_{t2rp}$ and $DSAFill_{t3rp}$ consist of pixels having peak contrast pixel values and "blank" pixels, which do not reflect any structure.

Known processing techniques may be applied to the DSA frames in order to remove noise, which may be accentuated due to the use of peak contrast pixel values. Such processing may also or alternatively adjust brightness, collimate the field of view, and/or conform the frames to the display properties of the display device of terminal 30.

Figure 8:
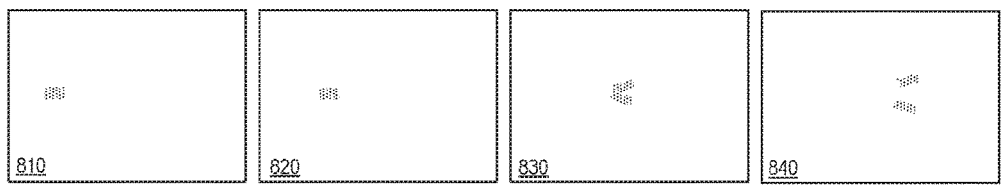
FIG. 8 illustrates images generated according to some embodiments.

In some embodiments, the frames $DSAFill_{t1rp}$, $DSAFill_{t2rp}$ and $DSAFill_{t3rp}$ may be displayed in succession to illustrate locations of peak contrast levels over time. FIG. 8 shows such frames 810 through 840 according to some embodiments. Each of frames 810 through 840 includes "blank" pixels and pixels having peak contrast pixel values as described above.

Those in the art will appreciate that various adaptations and modifications of the above-described embodiments can be configured without departing from the scope and spirit of the claims. Therefore, it is to be understood that the claims may be practiced other than as specifically described herein.

What is claimed is:

1. A system comprising:
   an interface to:
      receive a plurality of fill frames of a patient volume, each of the plurality of fill frames depicting a contrast medium within the patient volume at a respective time;
   a processor to:
      identify, for each pixel location of the fill frames, a fill frame whose pixel at the pixel location is associated with a pixel value which represents a greater level of contrast medium than the pixel values of pixels at the pixel location within the others of the plurality of fill frames; and
      generate a peak contrast fill frame corresponding to each fill frame, the peak contrast fill frame corresponding to a given fill frame including, at pixel locations for which the given fill frame was identified, pixels associated with pixel values of the given fill frame; and a storage device to store the plurality of peak contrast fill frames.

2. A system according to claim 1, further comprising:
a display to successively display the plurality of peak contrast fill frames.

3. A system according to claim 2, further comprising:
an X-ray detector and an X-ray source operable to acquire the plurality of fill frames.

4. A system according to claim 3, further comprising a contrast injector to inject the contrast medium into the patient volume.

5. A system according to claim 1, the interface to receive a mask frame of the patient volume, where the mask frame does not depict the contrast medium; and
the processor to subtract the mask frame from each of the plurality of peak contrast fill frames to generate a plurality of subtraction fill frames.

6. A system according to claim 5, further comprising a display to successively display the plurality of subtraction fill frames.

7. A system according to claim 1, the interface to receive a mask frame of the patient volume, where the mask frame does not depict the contrast medium,
wherein the peak contrast fill frame corresponding to a given fill frame includes, at pixel locations for which the given fill frame was not identified, pixels associated with pixel values of the mask frame.

8. A system according to claim 7, the processor to subtract the mask frame from each of the plurality of peak contrast fill frames to generate a plurality of subtraction fill frames.

9. A system according to claim 8, further comprising a display to successively display the plurality of subtraction fill frames.

10. A method comprising:
receiving a plurality of fill frames of a patient volume, each of the plurality of fill frames depicting a contrast medium within the patient volume at a respective time;
identifying, for each pixel location of the fill frames, a fill frame whose pixel at the pixel location is associated with a pixel value which represents a greater level of contrast medium than the pixel values of pixels at the pixel location within the others of the plurality of fill frames;
generating a peak contrast fill frame corresponding to each fill frame, the peak contrast fill frame corresponding to a given fill frame including, at pixel locations for which the given fill frame was identified, pixels associated with pixel values of the given fill frame; and
storing the plurality of peak contrast fill frames.

11. A method according to claim 10, further comprising:
receiving a mask frame of the patient volume, where the mask frame does not depict the contrast medium; and
subtracting the mask frame from each of the plurality of peak contrast fill frames to generate a plurality of subtraction fill frames.

12. A method according to claim 11, further comprising successively displaying the plurality of subtraction fill frames.

13. A method according to claim 10, further comprising receiving a mask frame of the patient volume, where the mask frame does not depict the contrast medium,
wherein the peak contrast fill frame corresponding to a given fill frame includes, at pixel locations for which the given fill frame was not identified, pixels associated with pixel values of the mask frame.

14. A method according to claim 13, further comprising subtracting the mask frame from each of the plurality of peak contrast fill frames to generate a plurality of subtraction fill frames.

15. A method according to claim 14, further comprising successively displaying the plurality of subtraction fill frames.

16. A system comprising:
an X-ray detector and an X-ray source operable to:
acquire a mask frame of a patient volume, where the mask frame does not depict a contrast medium; and
acquire a plurality of fill frames, each of the plurality of fill frames depicting the contrast medium within a patient volume at a respective time;
a processor to:
register each of the plurality of fill frames against the mask frame to generate a plurality of registered fill frames;
identify, for each pixel location of the registered fill frames, a registered fill frame whose pixel at the pixel location is associated with a pixel value which represents a greater level of contrast medium than the pixel values of pixels at the pixel location within the others of the plurality of registered fill frames;
generate a peak contrast fill frame corresponding to each registered fill frame, the peak contrast fill frame corresponding to a given registered fill frame including, at pixel locations for which the given registered fill frame was identified, pixels associated with pixel values of the given registered fill frame, and including, at pixel locations for which the given fill frame was not identified, pixels associated with pixel values of the mask frame; and
subtract the mask frame from each of the plurality of peak contrast fill frames to generate a plurality of subtraction frames; and
a storage device to store the plurality of subtraction frames.

17. A system according to claim 16, further comprising:
a display to successively display the plurality of subtraction frames.

18. A system according to claim 16, the processor further to apply noise reduction processing to plurality of peak contrast fill frames prior to subtraction of the mask frame.

* * * * *